(12) United States Patent
Khalfin et al.

(10) Patent No.: US 11,428,546 B2
(45) Date of Patent: Aug. 30, 2022

(54) METHOD AND APPARATUS FOR SYNCHRONIZING MULTIPLE MAGNETIC TRACKING SYSTEMS

(71) Applicant: PENUMBRA, INC., Alameda, CA (US)

(72) Inventors: Igor Khalfin, Pleasanton, CA (US); Amir Rubin, Los Gatos, CA (US); Oded Y. Zur, Kochav-Yair (IL)

(73) Assignee: PENUMBRA, INC., Alameda, CA (US)

( * ) Notice: Subject to any disclaimer, the term of this patent is extended or adjusted under 35 U.S.C. 154(b) by 861 days.

(21) Appl. No.: 16/282,782

(22) Filed: Feb. 22, 2019

(65) Prior Publication Data

US 2019/0257672 A1 Aug. 22, 2019

Related U.S. Application Data

(60) Provisional application No. 62/634,179, filed on Feb. 22, 2018.

(51) Int. Cl.
| | |
|---|---|
| *G01D 5/20* | (2006.01) |
| *G01B 7/004* | (2006.01) |
| *A61B 5/103* | (2006.01) |
| *G01S 3/00* | (2006.01) |
| *A61B 5/11* | (2006.01) |
| *A61B 5/06* | (2006.01) |

(52) U.S. Cl.
CPC ............. *G01D 5/208* (2013.01); *A61B 5/062* (2013.01); *A61B 5/103* (2013.01); *A61B 5/11* (2013.01); *G01B 7/004* (2013.01); *G01S 3/00* (2013.01)

(58) Field of Classification Search
CPC ..................................................... G01D 5/208
See application file for complete search history.

(56) References Cited

U.S. PATENT DOCUMENTS

| | | | |
|---|---|---|---|
| 4,737,794 A | 4/1988 | Jones | |
| 9,459,124 B2 | 10/2016 | Khalfin et al. | |
| 10,162,177 B2 | 12/2018 | Pedrotti et al. | |
| 2009/0076746 A1* | 3/2009 | Higgins | ................. A61B 5/062 702/57 |

\* cited by examiner

*Primary Examiner* — Nabil H Syed
*Assistant Examiner* — Cal J Eustaquio
(74) *Attorney, Agent, or Firm* — Haley Guiliano LLP (57) ABSTRACT

A method and apparatus is disclosed for allowing a magnetic tracking system to detect, and operate in close proximity in the same physical environment with, additional magnetic tracking systems. The first user's magnetic tracking system that becomes active in the physical space becomes the master system, and assigns time slots for its own transmitting antennas to generate the magnetic field which is used to determine the position and orientation of the user's limbs relative to the user's head. The master system also determines when other magnetic tracking systems become active in the physical space and assigns to those systems identification codes and time slots for their transmitting antennas to generate a magnetic field so that the position and orientation of the user's hands relative to the user's head for each of those systems may be determined. By requiring each magnetic tracking system to operate in different time slots, there is no interference between the systems.

23 Claims, 5 Drawing Sheets

METHOD AND APPARATUS FOR SYNCHRONIZING MULTIPLE MAGNETIC TRACKING SYSTEMS

This application claims priority to Provisional Application No. 62/634,179, filed Feb. 22, 2018, which is incorporated by reference herein in its entirety.

FIELD OF THE INVENTION

The present invention relates generally to AC electromagnetic tracking systems, and more particularly to allowing multiple tracking systems to operate in the same physical area.

BACKGROUND OF THE INVENTION

AC electromagnetic magnetic trackers (herein referred to as "magnetic trackers" or "magnetic tracking devices") that determine the position and orientation of a sensor in a magnetic tracker with respect to a transmitter or vice versa, are well known to those of skill in the art. One such example, U.S. Pat. No. 4,737,794 ("the '794 patent"), teaches a "method and apparatus for determining remote object orientation and position with an electromagnetic coupling." It shows a transmitter comprising a plurality of radiating antennas, located at a source to provide a plurality of magnetic fields spanning three dimensional space and defining a source reference coordinate frame, and a receiver comprising a plurality of receiving antennas located on an object to be tracked for receiving that field. A processor receives the outputs from the receiving antennas and converts the received components of the transmitted magnetic fields into remote object position and orientation relative to the source reference coordinate frame. The antennas may be, for example, dipole antennas, loop antennas, or coil antennas (the term "coils" is used herein to include any such antennas).

The '794 patent, as well as the references therein, provide detailed descriptions of magnetic tracker architectures. Another example is H. Himberg, "Latency and Distortion Compensation in Augmented Environment Using Electromagnetic Trackers," Doctoral Dissertation, 2010, Virginia Commonwealth University, Richmond Va. 23284, USA. This publication contains extensive review and references on the current status of magnetic tracker technology.

In practice, the transmitter typically includes three radiating antennas, usually three orthogonal concentric coils, that emit either a time domain multiplexed signal (TDM) at one frequency, or a frequency domain multiplexed signal (FDM) with at least three frequencies. The receiver or sensor similarly typically includes three concentric orthogonal search coils.

Some common applications track a user for the purpose of allowing the user to be immersed in an augmented or virtual reality world that is displayed to the user, for example, on a head-mounted display (HMD). In some prior art embodiments, a transmitter may be located in a fixed position, such as on a frame of an airplane cockpit, on a floor or on the ground, in a local base station, video game console or other apparatus. A receiver or sensor of a magnetic tracking device forwards the sensed electromagnetic magnetic field parameters to a processor, which, using the known parameters of the transmitted electromagnetic field, determines the position and orientation of the tracking device relative to the base station from such information.

In some prior art embodiments, it is possible to track movement of a user's hands and/or feet relative to the user's head so as to provide the perception that the user can see his or her own hands and/or feet in an augmented or virtual reality world. If a virtual reality world is configured appropriately, this can allow the user to interact with the virtual reality world as if the user is actually present there. See, for example, U.S. Pat. No. 10,162,177, assigned to the applicant of the current application.

Further, in various applications it may be desirable to have multiple users operating in a common physical space, with each user tracking, the movement of his or her own hands and/or feet or tools or devices held in the user's hands.

Current magnetic tracking systems lack the ability to autonomously detect the presence of another AC tracker in their proximity and have no means to operate in close physical proximity to similar systems without interference.

It is desirable to be able to allow magnetic tracking systems to operate in close proximity in the same physical environment with additional magnetic tracking systems.

SUMMARY OF THE INVENTION

A system and method is disclosed that allows a magnetic tracking system to detect, and operate in close proximity in the same physical environment with, one or more additional magnetic tracking systems without interference.

The first magnetic tracking system of a user that becomes active in the physical space becomes the master system, and assigns time slots for its own transmitting antennas to generate the magnetic field which is used to determine the position and orientation of the user's limbs relative to the user's head. The master system also determines when other magnetic tracking systems become active in the physical space and assigns to those systems identification codes and time slots for their transmitting antennas to generate a magnetic field so that the position and orientation of the user's hands relative to the user's head for each of those systems may be determined. In one embodiment, each tracking system operates in different time slots.

DETAILED DESCRIPTION OF THE INVENTION

A system and method is disclosed that allows a magnetic tracking system to identify the presence of other similar magnetic tracking systems and to operate in close proximity in the same physical environment with one or more additional magnetic tracking systems.

The system and method allows operation of multiple systems by having one system (usually, the first system introduced to the physical space) assume the role of "master" system upon boot-up and begin broadcasting synchronization signals. If a master system is already present, any other system entering into the physical space assume the role of "slave" by having each system at boot-up check to see if there is another system broadcasting synchronization signals; if so, the new system requests an ID from the broadcasting system. The master system, receiving the request from the new system, assigns the new system a new, slave, ID and a time slot in which the new slave system can operate. If the master system is turned off or leaves the area, the first slave system that recognizes it is not receiving the ID or synchronization signal from the master becomes the master system and begins broadcasting synchronization signals.

The identification and synchronization communication between the master system and slave systems operates in a manner other than on the generated magnetic field frequencies used to track position and orientation. Rather, such communication between systems occurs over a different, non-conflicting communication channel such as infrared (IR) or radio frequency (RF) link (herein the "synchronization link"). Such a link will typically include appropriate IR or RF hardware and logic that transmits a unique system code and listens for the presence of other such codes.

Figure 5:
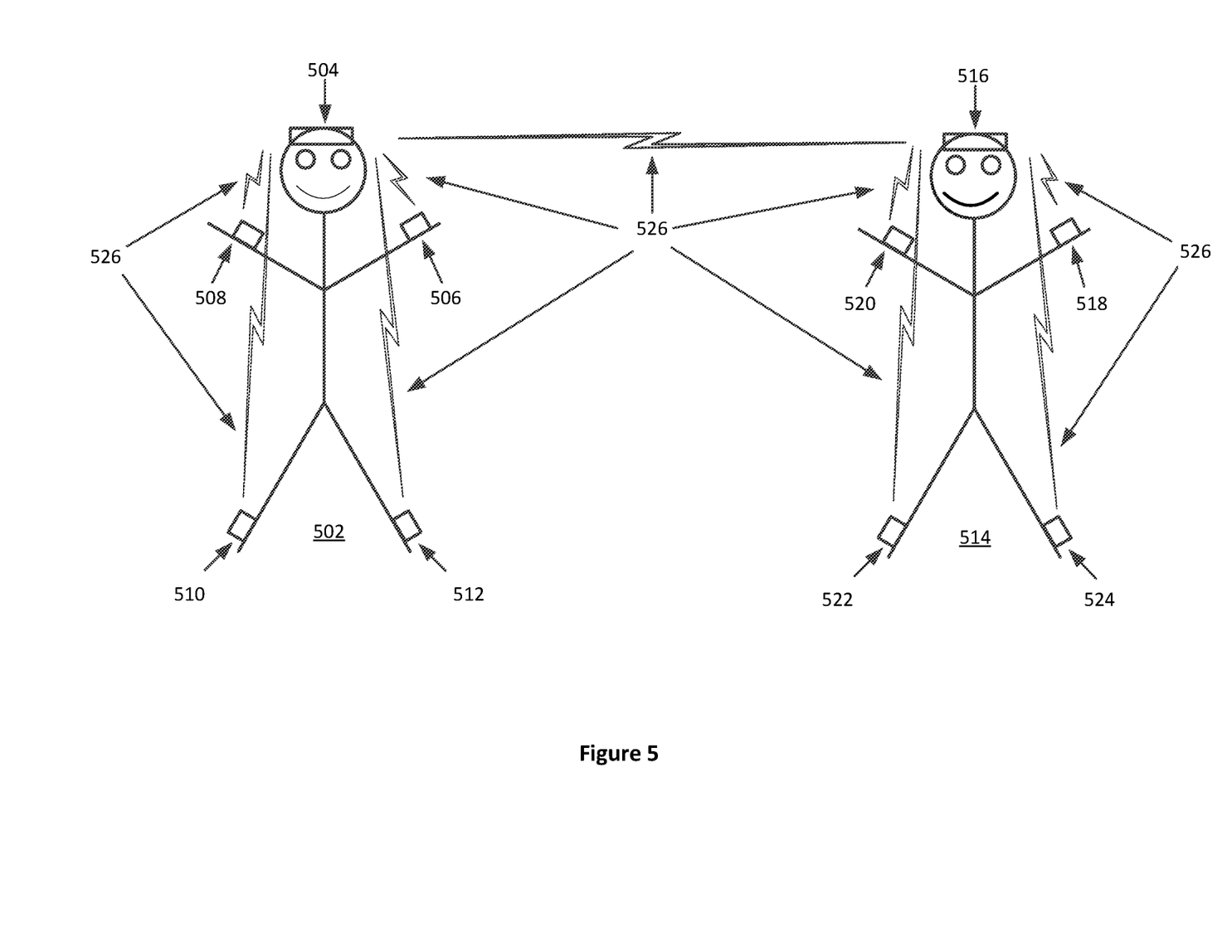
FIG. 5 is an illustration of two users, each wearing a magnetic tracking system containing a headset and multiple handsets on the user's body, according to one embodiment.

As illustrated in some embodiments, each user wears a magnetic tracking system containing a headset, and one or more tracking devices, herein called "handsets," which are attached to the user or placed in a user desired or system specified location in the physical environment. As illustrated, user 502 wears a headset 504, as well as four different handsets attached to the user's limbs. Handset 506 is attached to the left hand or arm of user 502, handset 508 to the right hand or arm, handset 510 to the right foot or leg, and handset 512 to the left foot or leg. User 514 similarly wears a headset 516 and handsets 518, 520, 522 and 524. Although FIG. 5 illustrates two users, in some embodiments there may be more than two users.

In the description herein, it is assumed that a user holds or wears a handset on each hand. However, a user may wear one handset, or more than two; for example, as seen in FIG. 5, a user might wear four handsets, one on each hand and one on each foot, or some other number of handsets if it is desired to track some other part of the user's body, or even some other object.

Each user's handsets operate as magnetic transmitters, otherwise known as sources, by having radiating antennas (coils) for generating a plurality of magnetic fields; each headset contains a receiver, otherwise known as a sensor, comprising a plurality of receiving antennas (coils) for sensing the magnetic fields. Each user also typically has a HMD that displays the virtual or augmented reality world or alphanumeric information; in some embodiments the HMD is also located in the headset. The headset and handsets also contain the IR or RF hardware necessary for synchronization links 526 function between the headset 504 and handsets 506, 508, 510 and 512 on user 1, between the headset 516 and handsets 518, 520, 522 and 524 on user 2, and between headset 504 of user 1 and headset 516 of user 2, as described herein.

It is well known in the art that such transmitters can be put in stationary positions, with headsets and handsets containing just receivers or sensors, or a transmitter can be placed on a MID and sensors on handsets and body parts. In any of these cases such a system will require just the reference frame transformations that are well known in the art.

In operation, using techniques known in the art, the sensor or sensors detects the magnetic field generated by the transmitter or transmitters and provides the transmitter-sensor transfer function (i.e., the sensor measures a response to the magnetic field generated by the transmitter) to a processor that produces a position and orientation solution for the sensor with respect to the transmitter. This is done for each transmitter-sensor combination. It is known in the art that a transmitter-to-sensor position and orientation solution is just an inverse transformation of the original solution.

As above, a given transmitter/receiver (sensor) pair typically uses a "set" of three frequencies that are orthogonal in the Fourier sampling space to determine the position and orientation of the receiver relative to the transmitter. It is possible to have multiple sets of frequencies in some embodiments; for example, a single system with a headset and two handsets could use two sets of frequencies, i.e., six frequencies in total, one set of frequencies for each of the two handsets.

However, there is a practical limit to the number of frequencies that may be used. Further, it is desirable to minimize the number of frequencies so that they may be separated enough in frequency to avoid crosstalk.

Thus, when each of multiple users has two or more handsets, if it is desired that each handset use three frequencies that are different from all other handsets, the number of frequencies needed multiplies very quickly. It is likewise desirable to have multiple users' systems use the same frequency for ease of manufacturing and to avoid increasing the operational bandwidth beyond the practical limits. For these reasons, it is preferable to have every handset to transmit the same three frequencies (or at the very least to limit the number of sets of frequencies) and find another way to distinguish which handset is generating which magnetic fields.

This may be accomplished by creating time "slots," i.e., distinct time periods, and assigning to each transmitter a different time slot during which the transmitter should generate the magnetic field. By communicating to each user's headset the time slots during which the user's handsets should generate the magnetic field, each sensor in a headset can then sense the magnetic field from each of its handsets during the appropriate time slot and thus obtain the data from which the position of the handsets relative to the headset may be determined. The time slots periodically repeat so that each user's headset senses the magnetic fields from the same user's handsets at regular intervals.

The time slots must be long enough to allow the magnetic field to be generated and properly sensed; a certain number of samples of the magnetic field are required to accurately obtain position and orientation. What constitutes a sufficient time slot length is thus largely determined by the signal-to-noise ratio of the sensed magnetic field, i.e., a better signal-to-noise ratio allows for shorter time slots. In addition, the time slots are preferably short enough that the intervals at which each handset's generated magnetic field is sensed will result in apparent motion to the user that is relatively continuous.

A standalone electromagnetic tracking system with multiple transmitters but only one sensor, described in U.S. Pat. No. 9,459,124, may help illustrate some of the requirements for multiple systems working in the same physical environment. Assume that the frame rate of the system is 240 frames per second (FPS). The sampling rate in this case is 192,000 samples per second (i.e., 192 KHz), or 800 samples per data frame. If there are four total transmitters in this example, each transmitter's magnetic field is thus sensed every 1/240 of a second sequentially, thus providing a 1/60 of a second refresh rate. (Alternatively, the data frame may be 1/4 of the original envelope, i.e., 200 samples per frame, maintaining the same total 240 frames per second rate).

Figure 1:
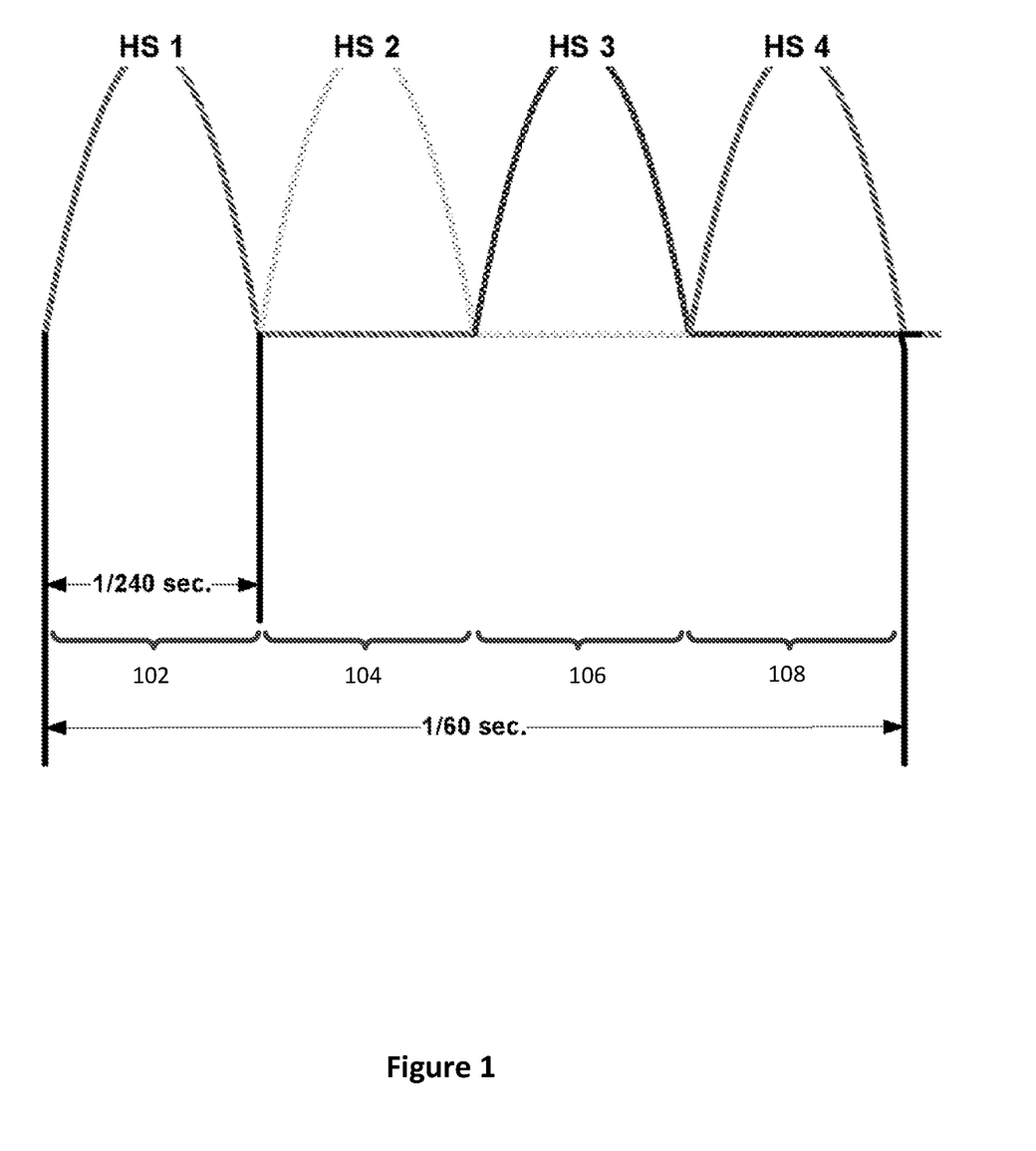
FIG. 1 is a timing diagram of the magnetic field signal envelopes from multiple transmitters working on the same frequencies according to one embodiment.

To minimize transients, all frequencies of a given transmitter are multiplied to the common window, containing cos^2 or the Hamming window during 1/4 of the common envelope and zeroes during 3/4 of the envelope. Envelopes in each of the transmitters of the handsets are shifted by 1/4 of the common envelope length that is defined by the handset/transmitter ID, i.e., HS1 to HS4. Note that 2 frequency sets (2×3 frequencies) can work with 8 transmitters with the same data rate as illustrated.

FIG. 1 illustrates how multiple transmitters can be used together with such time slots. For example, assume that there are two handsets assigned to a first, or master, magnetic tracking system, designated as HS1 and HS2, and two handsets assigned to a second, or slave, magnetic tracking system, designated as HS3 and HS4. In the illustration of FIG. 1, HS1 generates its magnetic field in the first 1/240 of a second 102, HS2 generates its magnetic field in the second 1/240 of a second 104, HS3 in the third 1/240 of a second 106, and HS4 in the fourth 1/240 of a second 108, adding up to 1/60 of a second.

This sequence is then to be repeated in the next 1/60 of a second, so that each handset generates its magnetic field every 1/60 of a second, allowing the position and orientation of each handset to be updated every 1/60 of a second.

Alternatively, if the signal-to-noise ratio is sufficient, the time slots may be of a shorter duration. One of skill in the art will be able to decide upon an appropriate combination of time slot duration and refresh rate for a given situation.

Prior art magnetic tracking systems have no means to detect other systems autonomously. One of skill in the art will appreciate, in light of the teachings herein, that the individual magnetic tracking systems for each user should know about other systems and be synchronized, since each system operates using its own timing.

Thus, in some embodiments, the master system will preferably periodically generate and transmit a synchronization signal to the slave systems, so that all of the tracking systems will recognize the beginning of each time slot and each handset will be able to generate its magnetic field during its assigned time slot without overlapping with the magnetic field from another handset. This synchronization signal itself will preferably be very short and thus done quickly, preferably in a single sampling interval, which as above in this embodiment is 1/192,000 of a second, about 5 microseconds, and often enough that drift will not become a problem. The synchronization signal may in some cases be generated, for example, at the beginning of every time slot, or possibly at longer intervals if desired. For example, it may be sufficient to provide a synchronization signal every 1/60 of a second (e.g., the beginning of the period cycle of time slots rather than at the beginning of each individual time slot), or even more infrequently.

As above, the master system transmits the synchronization and identification signals to the slave systems by a different mechanism than the magnetic fields, for example, by IR or RF, so as to avoid using the magnetic fields for any purpose other than determining position and orientation, which might, for example, impair efforts at correction of distortion in the magnetic fields.

Figure 2:
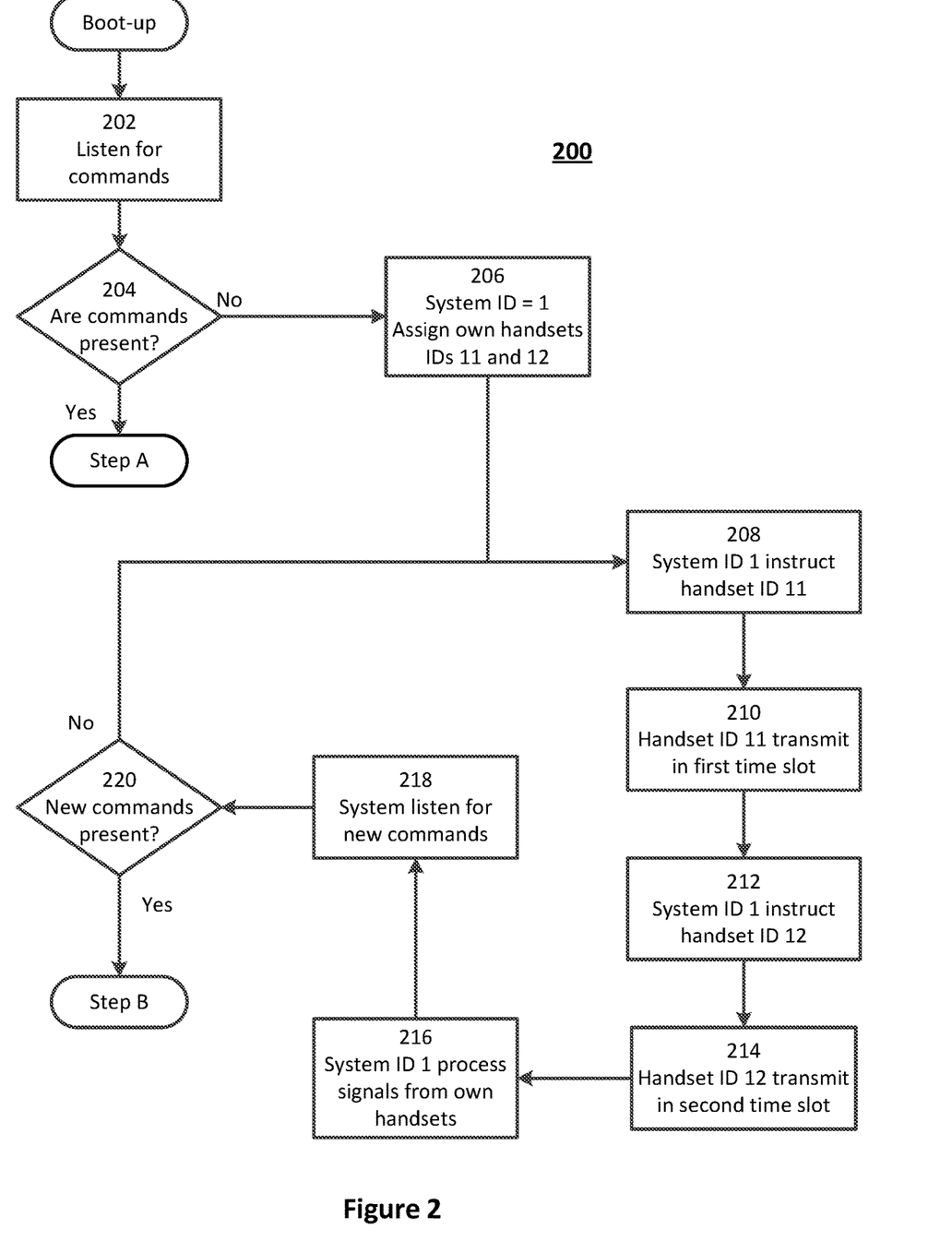
FIG. 2 is a flow chart of the operation of the boot-up sequence of the first magnetic tracking system introduced into a physical space according to one embodiment.
Figure 3:
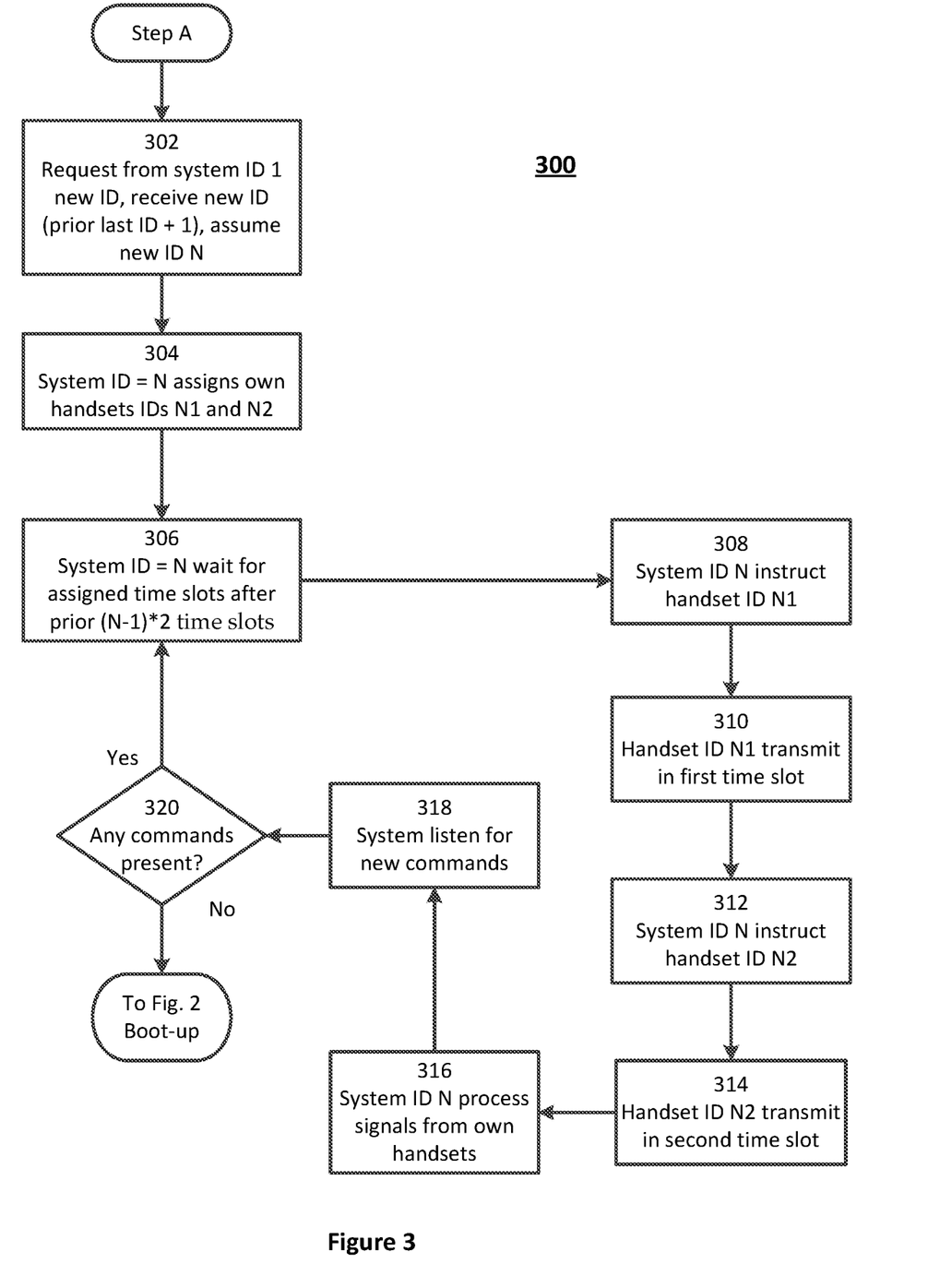
FIG. 3 is a flow chart of the operation of a magnetic tracking system introduced into the physical space if other systems are present according to one embodiment.
Figure 4:
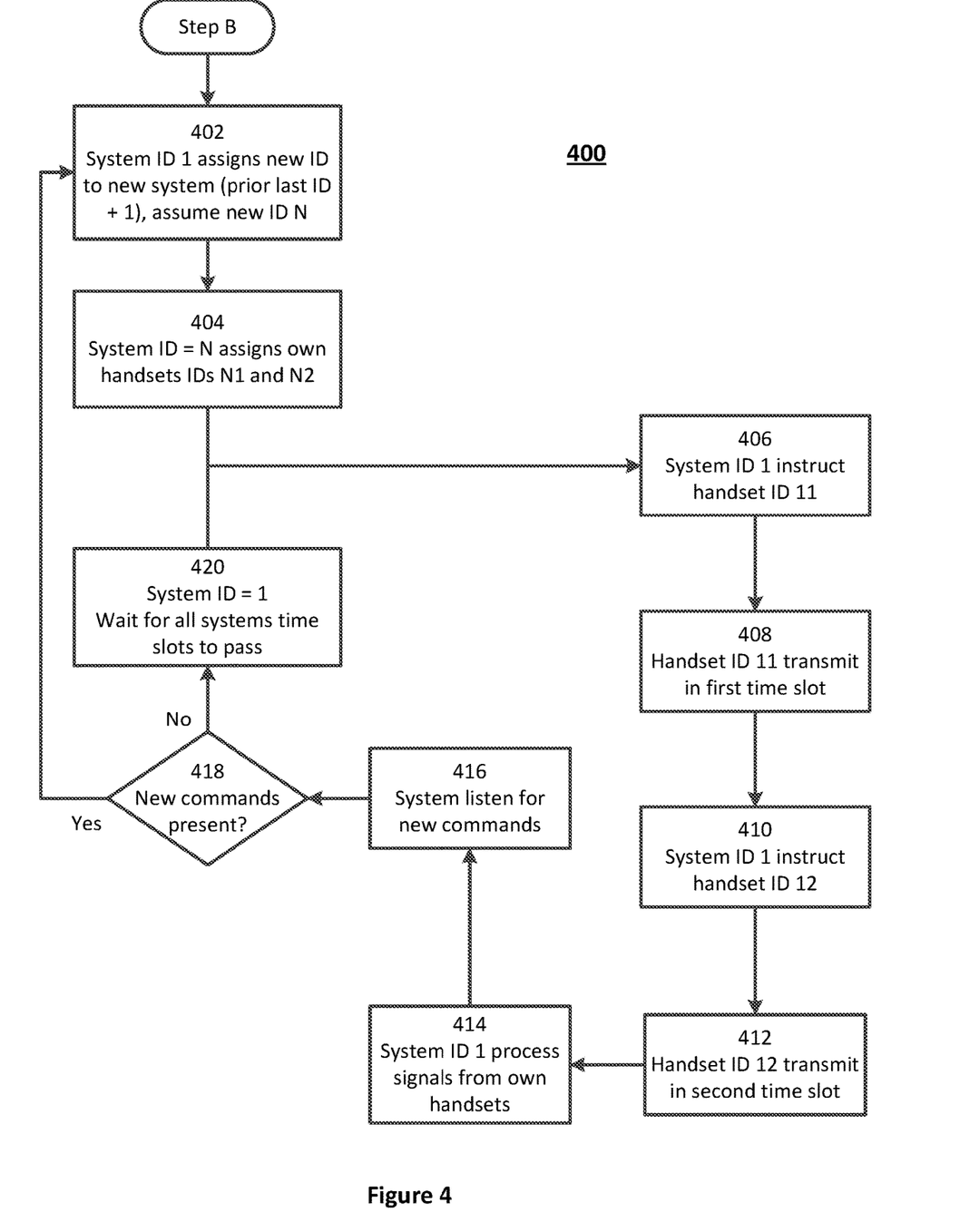
FIG. 4 is a flow chart of the multi-user operations of the first magnetic tracking system when one or more additional magnetic systems have entered into the physical space according to one embodiment.

FIGS. 2 to 4 show the operation of a magnetic tracking system under various conditions. FIG. 2 is a flow chart of the process 200 of the boot-up sequence of a magnetic tracking system upon becoming active in a physical space. (As used herein, the term "boot-up" includes any type of activation or start-up process.) After the system is activated, at step 202 the system (the logic may be in the headset) checks to see if there are one or more other systems in the area providing commands or synchronization signals (collectively "commands"). In one embodiment, this is done by the system checking the receiver of the synchronization link. If at step 204 the system determines that commands from another system are present, i.e., that this system is not the first system present, the process proceeds to the process of FIG. 3 described below.

If at step 204 the system determines that no commands from another system are present, at step 206 the system designates itself as the master system and designates its handsets accordingly. In one embodiment this is done by the system giving itself the identification (ID) of 1, i.e., that it is the master system, and designates its handsets as IDs 11 and 12, i.e., that they are the first and second handsets of the master system. At step 208, the system instructs, via the synchronization link, the handset designated as ID 11 to generate the magnetic field during the first time slot, in this example the first 1/240 of a second, and at step 210 handset 11 generates its magnetic field.

Similarly, at step 212, the system instructs, via the synchronization link, its handset ID 12 to generate the magnetic field during the second time slot, in this example the second 1/240 of a second, and at step 214 handset ID 12 generates its magnetic field. At step 216, the data from the handsets is processed to determine and output the position and orientation of the handsets.

At step 218, as was done in step 202, the system again checks to see if there is another system in the area providing commands, i.e., if another system has become active. If at step 220 the system does not find any other system, it returns to step 208 and again asks for the handsets to sequentially generate magnetic fields as above.

If at step 220 the system does find that there is another system that has broadcast its presence and is providing commands, it proceeds to the continuous process shown in FIG. 4 described below.

FIG. 3 is a flow chart of the process 300 of operation of a magnetic tracking system upon becoming active in the physical space once the system has determined that it is not the first, master system. As above, upon boot-up, at step 204 of FIG. 2 the system has previously determined that there is another system already active in the area.

At step 302, using the synchronization link, the second new system requests that it be assigned a slave ID by the previously present master system, i.e., the system with ID 1. The master system will assign the next available ID, i.e., if only the master system was previously present the new system will be given the slave ID 2, if two systems were previously present the new system will be given the slave ID 3, etc. Here it is generalized that N−1 systems were previously present, and the new system is given the slave ID N.

At step 304 the system now designated as slave ID N assigns to its associated handsets appropriate IDs, which in one embodiment results in them being given the IDs N1 and N2.

At step 306, the new system now given slave ID N waits for its turn. In one embodiment, this means determining when the next two time slots, i.e., the two time slots that occur after all of the other handsets present in the space have activated their radiating antennas during their assigned time slots, will occur and waiting for these time slots. These will be the two time slots after (N−1)*2 time slots, i.e., two time slots for each of the previously active N−1 systems.

At step 308, the system N sends a command to handset N1 to generate its magnetic field during the first of the two time slots assigned to system N, and the handset N1 does so at step 310. Similarly, at step 312 the system N sends a command to handset N2 to generate its magnetic field during the second of the two assigned time slots, and the handset N2 does so at step 314.

At step 316 the data from the handsets is processed to determine position and orientation of the handsets. In one embodiment this processing is done by a processor in the headset of system ID N to determine position and orientation of handsets N1 and N2.

At step 318, the system listens for new commands, and at step 320 determines whether it is still receiving commands (i.e., synchronization signals) from the master system. If the system is still receiving commands, it then returns to step 306 to wait for its next two assigned time slots.

If at step 320 the system determines that is has not received a synchronization signal for a predetermined period of time (e.g., one that is longer than the expected interval between synchronization signals), the system returns to the boot-up sequence of FIG. 2, as described elsewhere herein.

FIG. 4 is a flow chart of the process 400 of continuous operation of the master system when two or more systems are present in the physical space.

At step 220 in process 200 of FIG. 2 described above, the master system determined that there were now one or more other systems present in the physical space. At step 402, the master system assigns to each new system a new slave ID, starting with the next number above the number of systems previously present; thus, if this is the first time that process 400 has been reached, following the processes of FIGS. 2 and 3 described above, the next new system will be given slave ID 2, and subsequent newly present systems will get higher slave ID numbers.

At step 404, as in step 304 of process 300 in FIG. 3 described above, a newly present system given slave ID N will assign its own handsets the IDs N1 and N2, and determine the two time slots that it is to use for its handsets. The master system adjusts for the new time slots in the timing sequence, such as that shown in FIG. 1 above, so that it can delay the next magnetic field transmissions of its own handsets appropriately.

As in steps 208 and 210 of process 200 in FIG. 2 above, at step 406, the master system ID 1 instructs the handset designated as ID 11 to generate the magnetic field during the first time slot, in this example the first ¹⁄₂₄₀ of a second, and handset ID 11 does so at step 408.

Similarly, as in steps 212 to 216 of process 200, at step 410, the master system ID 1 instructs its handset ID 12 to generate the magnetic field during the second time slot, in this example the second ¹⁄₂₄₀ of a second, and the handset ID 12 does so at step 412. At step 414, the data from its handsets IDs 11 and 12 are then processed to determine position and orientation of handsets IDs 11 and 12. In one embodiment this processing is done by a processor in the headset of master system ID 1.

At step 416, the master system having ID 1 again listens for still more new commands, and at step 418 determines whether new commands are present. If there are more new commands, this indicates that there are new systems that have not yet received an ID, and the process returns to step 402.

If no new commands are present, then at step 420 the headset ID 1 waits for all of the time slots assigned to other systems to pass, and then returns to step 406 to command its own handsets to transmit their magnetic fields as described above.

The processes of FIGS. 2 to 4 will continue to repeat as long as any of the magnetic tracking systems remain active.

In some cases the master system may leave the environment, or for some reason may stop operating (e.g., it may be turned off by its user). In such situations it is not necessary that the slave systems stop operating, and instead one of the slave systems can then become the master and take over management of the other slave systems.

In some embodiments this may be accomplished by having the first slave system to recognize that the master system is no longer active take over as a new master. Such recognition may, for example, occur as in step 310 of process 300 of FIG. 3 above, when a slave system does not receive a synchronization signal for a predetermined period of time that is longer than the expected interval between synchronization signals. In this case, the system that has first recognized the absence of a master system returns to the boot-up sequence of process 200 of FIG. 2 and becomes the new master system.

In the above-described embodiments, the handsets contain the radiating antennas that generate the magnetic field, and the headsets contain the receivers that sense the magnetic field. One of skill in the art will appreciate that some prior art systems place the radiating antennas on the head (e.g., in a headset), and receiver(s) in the handsets or handheld controllers. While this may be done and still be consistent with the above description, it is believed that users will prefer placing the radiating antennas in the handsets. The radiating antennas, along with the required power supply, are generally heavier than the sensors, and may not be comfortable for users when located on their heads. Further, there is at least a perception that generating magnetic fields near the head can be problematic by potentially causing medical problems for the user.

By allowing one magnetic tracking system to act as the master system and assign time slots for its own handsets to generate their magnetic fields, and to assign time slots to one or more other slave systems for their handsets to generate their magnetic fields, the described method and apparatus allows multiple magnetic tracking systems to operate in physical proximity to one another. As above, if desired, all of the magnetic tracking systems are able to operate using the same set of orthogonal frequencies for the generation of the magnetic fields, without interference between the different systems.

The disclosed system and method has been explained above with reference to several embodiments. Other embodiments will be apparent to those skilled in the art in light of this disclosure. Certain aspects of the described method and apparatus may readily be implemented using configurations or steps other than those described in the embodiments above, or in conjunction with elements other than or in addition to those described above. It will also be apparent that in some instances the order of steps described herein may be altered without changing the result of performance of all of the described steps.

As above, in some embodiments it may be desirable to use more than one set of three frequencies, so that more than one handset can generate a magnetic field during a time slot, thus allowing more systems to operate within the same physical space while maintaining the refresh rate. For example, also as above, using two sets of distinct frequencies in a given system will allow two handsets to generate magnetic fields in the same time slot without interference between the magnetic fields, and thus double the number of systems that can operate simultaneously. However, also as above, using too many frequencies can cause crosstalk and degrade performance. One of skill in the art will be able to decide the relative merits of using different numbers of frequencies in a particular case.

There may be a single processor in each magnetic tracking system, or multiple processors performing the different functions described herein. In some embodiments one or more processors may be situated in another location, and communicate with one or more of the magnetic tracking systems via the identification and synchronization channel. In light of the teachings herein, one of skill in the art will appreciate how to determine which and how many processors will be appropriate for a specific intended application, and where in a given system they might be located.

It should also be appreciated that the described method and apparatus can be implemented in numerous ways, including as a process, an apparatus, or a system, or as a combination of all of the above. The methods described herein may be implemented by program instructions for instructing a processor to perform such methods, and such instructions recorded on a non-transitory computer readable storage medium such as a hard disk drive, floppy disk, optical disc such as a compact disc (CD) or digital versatile disc (DVD), flash memory, etc. It may be possible to incorporate the described methods into hard-wired logic if desired. It should be noted that the order of the steps of the methods described herein may be altered and still be within the scope of the disclosure.

These and other variations upon the embodiments are intended to be covered by the present disclosure, which is limited only by the appended claims.

What is claimed is:

1. A system for allowing two magnetic tracking systems to operate in the same physical environment, comprising:
    first and second magnetic tracking systems, each magnetic tracking system comprising;
        one or more tracking devices, each tracking device containing a plurality of source magnetic coils configured to generate a magnetic field;
        a receiver containing a plurality of sensor magnetic coils configured to sense the magnetic field and generate magnetic sensor data;
        a communication link for communicating between the receiver and the one or more tracking devices, and between the first and second magnetic tracking systems, the communication link operating in a manner other than on the generated magnetic field;
        a processor configured to:
            determine from the communication link whether the magnetic tracking system is a first system of the first and second magnetic tracking systems to be active in the same physical environment;
            when the magnetic tracking system is the first of the first and second magnetic tracking systems to be active in the same physical environment:
                assign the magnetic tracking system a master identification;
                generate and transmit a synchronization signal corresponding to a series of time slots;
                sequentially instruct, using the communication link, the one or more tracking devices to each generate a magnetic field during a different time slot in the series of time slots; and
                determine that the other of the first and second magnetic tracking systems has requested a slave identification, and assign the other of the first and second magnetic tracking systems a slave identification from which the other of the first and second magnetic tracking systems can determine further sequential time slots during which the one or more tracking devices in the other of the first and second magnetic tracking systems are to generate a magnetic field;
            when the magnetic tracking system is not the first of the first and second magnetic tracking systems to be active in the same physical environment:
                request, using the communication link, from the other of the first and second magnetic tracking systems a slave identification from which further time slots in the series of time slots for generating a magnetic field can be determined;
                receive, using the communication link, from the other of the first and second magnetic tracking systems the synchronization signal; and
                sequentially instruct, using the communication link, the one or more tracking devices to each generate a magnetic field during a different time slot in the series of time slots;
            and
            determine the position and orientation of the one or more tracking devices relative to the receiver from the magnetic sensor data.

2. The system of claim 1 wherein the processor configured to determine whether the magnetic tracking system is the first system of the first and second magnetic tracking systems to be active in the same physical environment by determining whether the other of the first and second magnetic tracking systems is communicating using the communication link.

3. The system of claim 1 wherein the receiver is further configured to be attached to the head of the user.

4. The system of claim 1 wherein the one or more tracking devices are further configured to be attached to limbs of the user.

5. The system of claim 1 wherein the one or more tracking devices are configured to be placed in a location in the same physical environment.

6. The system of claim 1 wherein the communication link is an infrared optical communication device.

7. The system of claim 1 wherein the communication link is a radio frequency communication device.

8. The system of claim 1 wherein the receiver is located in a headset configured to be attached to the user's head.

9. The system of claim 1 wherein each of the one or more tracking devices is located in a handset configured to be attached to a limb of the user.

10. The system of claim 1 wherein the processor is further configured to:
    determine, when the magnetic tracking system has been assigned a slave identification, that the processor has not received a synchronization signal for a predetermined period of time;
    assign the magnetic tracking system a master identification;
    generate and transmit a synchronization signal corresponding to a series of time slots; and
    sequentially instruct, using the communication link, the one or more tracking devices to each generate a magnetic field during a different time slot in the series of time slots.

11. The system of claim 1 wherein the processor configured to generate and transmit the synchronization signal is further configured to generate and transmit the synchronization signal at periodic intervals.

12. A method of allowing two magnetic tracking systems to operate in the same physical environment, each magnetic tracking system comprising one or more tracking devices, each tracking device containing a plurality of source magnetic coils configured to generate a magnetic field, a receiver containing a plurality of sensor magnetic coils configured to sense the magnetic field and generate magnetic sensor data, a communication link for communicating between the receiver and the one or more tracking devices, and between the first and second magnetic tracking systems, the communication link operating in a manner other than on the generated magnetic field, and a processor, the method comprising;

determining by the processor from the communication link whether the magnetic tracking system is a first system of the first and second magnetic tracking systems to be active in the same physical environment;

when the magnetic tracking system is the first of the first and second magnetic tracking systems to be active in the same physical environment:

assigning, by the processor, the magnetic tracking system a master identification;

generating and transmitting a synchronization signal corresponding to a series of time slots;

sequentially instructing, by the processor using the communication link, the one or more tracking devices to each generate a magnetic field during a different time slot in the series of time slots; and determining by the processor that the other of the first and second magnetic tracking systems has requested a slave identification, and assign the other of the first and second magnetic tracking systems a slave identification from which the other of the first and second magnetic tracking systems can determine further sequential time slots during which the one or more tracking devices in the other of the first and second magnetic tracking systems are to generate a magnetic field;

when the magnetic tracking system is not the first of the first and second magnetic tracking systems to be active in the same physical environment:

requesting by the processor from the other of the first and second magnetic tracking systems a slave identification from which further sequential time slots for generating a magnetic field can be determined;

receiving, using the communication link, from the other of the first and second magnetic tracking systems the synchronization signal; and instructing, by the processor using the communication link, the one or more tracking devices to sequentially generate a magnetic field during the determined further sequential time slots;

and determining by the processor the position and orientation of the one or more tracking devices on the user relative to the receiver from the magnetic sensor data.

13. The method of claim 12 wherein determining by the processor whether the magnetic tracking system is the first system of the first and second magnetic tracking systems to be active in the same physical environment is done by determining whether the other of the first and second magnetic tracking systems is communicating using the communication link.

14. The method of claim 12 wherein the receiver is further configured to be attached to the head of the user.

15. The method of claim 12 wherein the one or more tracking devices are further configured to be attached to limbs of the user.

16. The method of claim 12 wherein the one or more tracking devices are further configured to be placed in a location in the same physical environment.

17. The method of claim 12 wherein the communication link is an infrared optical communication device.

18. The method of claim 12 wherein the communication link is a radio frequency communication device.

19. The method of claim 12 wherein the receiver is located in a headset configured to be attached to the head of the user.

20. The method of claim 12 wherein each of the one or more tracking devices is located in a handset configured to be attached to a limb of the user.

21. The method of claim 12 further comprising:

determining, when the magnetic tracking system has been assigned a slave identification, that the processor has not received a synchronization signal for a predetermined period of time:

assigning the magnetic tracking system a master identification;

generating and transmitting a synchronization signal corresponding to a series of time slots; and sequentially instructing, using the communication link, the one or more tracking devices to each generate a magnetic field during a different time slot in the series of time slots.

22. The method of claim 12, further comprising generating and transmitting, by the processor, the synchronization signal at periodic intervals.

23. A non-transitory computer readable storage medium having embodied thereon instructions for causing a computing device to execute a method of allowing two magnetic tracking systems to operate in the same physical environment, each magnetic tracking system comprising one or more tracking devices, each tracking device containing a plurality of source magnetic coils configured to generate a magnetic field, a receiver containing a plurality of sensor magnetic coils configured to sense the magnetic field and generate magnetic sensor data, a communication link for communicating between the receiver and the one or more tracking devices on the user, and between the first and second magnetic tracking systems, the communication link operating in a manner other than on the generated magnetic field, and a processor, the method comprising:

determining by the processor from the communication link whether the magnetic tracking system is a first system of the first and second magnetic tracking systems to be active in the same physical environment, when the magnetic tracking system is the first of the first and second magnetic tracking systems to be active in the same physical environment:

assigning, by the processor, the magnetic tracking system a master identification;

generating and transmitting a synchronization signal corresponding to a series of time slots;

sequentially instructing, by the processor using the communication link, the one or more tracking devices to each generate a magnetic field during a different time slot in the series of time slots; and determining by the processor that the other of the first and second magnetic tracking systems has requested a slave identification, and assign the other of the first and second magnetic tracking systems a slave identification from which the other of the first and second magnetic tracking systems can determine further sequential time slots during which the one or more tracking devices in the other of the first and second magnetic tracking systems are to generate a magnetic field; when the magnetic tracking system is not the first of the first and second magnetic tracking systems to be active in the same physical environment:

requesting by the processor from the other of the first and second magnetic tracking systems a slave identification from which further sequential time slots for generating a magnetic field can be determined;

receiving, using the communication link, from the other of the first and second magnetic tracking systems the synchronization signal, and instructing, by the processor using the communication link, the one or more tracking devices to sequentially generate a magnetic field during the determined further sequential time slots; and determining by the processor the position and orientation of the one or more tracking devices on the user relative to the receiver from the magnetic sensor data.

* * * * *